(12) United States Patent
Troczynski et al.

(10) Patent No.: US 6,770,325 B2
(45) Date of Patent: Aug. 3, 2004

(54) PROCESS FOR MAKING CHEMICALLY BONDED COMPOSITE HYDROXIDE CERAMICS

(75) Inventors: Tomasz Troczynski, Vancouver (CA); Quanzu Yang, Vancouver (CA)

(73) Assignee: The University of British Columbia, Vancouver (CA)

( * ) Notice: Subject to any disclaimer, the term of this patent is extended or adjusted under 35 U.S.C. 154(b) by 79 days.

(21) Appl. No.: 10/083,589

(22) Filed: Feb. 27, 2002

(65) Prior Publication Data

US 2002/0107133 A1 Aug. 8, 2002

Related U.S. Application Data

(63) Continuation-in-part of application No. 09/574,237, filed on May 19, 2000.

(51) Int. Cl.$^7$ .............................. B05D 3/02; B05D 1/36; B05D 1/18
(52) U.S. Cl. ................. 427/376.2; 427/379; 427/419.2; 427/430.1; 427/443.2
(58) Field of Search .............................. 427/376.2, 379, 427/419.2, 430.1, 443.2

(56) References Cited

U.S. PATENT DOCUMENTS

| | | | |
|---|---|---|---|
| 3,248,251 A | 4/1966 | Allen | |
| 3,395,027 A | 7/1968 | Klotz | |
| 3,547,670 A | * 12/1970 | Fuchs et al. ............. | 427/372.2 |
| 3,789,096 A | 1/1974 | Church et al. | |
| 4,544,408 A | 10/1985 | Mosser et al. | |
| 4,838,942 A | 6/1989 | Puchinger et al. | |
| 4,927,673 A | 5/1990 | Buntrock et al. | |
| 5,178,846 A | 1/1993 | Buelow et al. | |
| 5,279,649 A | 1/1994 | Stetson et al. | |
| 5,279,650 A | 1/1994 | Stetson et al. | |
| 5,478,413 A | 12/1995 | Mosser et al. | |
| 5,573,986 A | * 11/1996 | Talmy et al. ............... | 501/95.3 |
| 5,585,136 A | 12/1996 | Barrow et al. | |
| 5,652,064 A | 7/1997 | Mosser et al. | |
| 5,803,990 A | 9/1998 | Mosser et al. | |
| 5,968,240 A | 10/1999 | Myers et al. | |
| RE36,573 E | 2/2000 | Barrow et al. | |

OTHER PUBLICATIONS

W.D. Kingery. "Fundamental Study of Phosphate Bonding in Refractories: Parts I. II, III". *J. Am. Cer. Soc.* 33 (1950) 239–50.
J. Cassidy, "Phosphate Bonding Then and Now", *Am. Cer. Soc. Bull.* 56 (1977) 640–43.
J.V. Bothe, Jr., et al., "Low–Temperature Formation of Aluminum Orthophosphate", *J. Am. Cer. Soc.* 76 (1993) 362–68.
J.V. Bothe, Jr., et al., "Reactivity of Lamina toward Phosphoric Acid", *J. Am. Cer. Soc.* 76 (1993) 2553–58.
S. Kwon, et al., "Sintering of Mixtures of seeded Boehmite and Ultrafine—Alumina", *J. Am. Cer. Soc.* 83 (2000) 82–88.
M. Kumagai, et al., "Controlled Transformation and Sintering of a Boehmite Sol–Gel—Alumina Seeding", *J. Am. Cer. Soc.* 68 (1985) 500–505.
D. A. Barrow, et al., "Thick ceramic coatings using a sol gel based ceramic–ceramic 0.3 composite", *Surf. Coat. Tech.*, 76–77 (1995) 113.

* cited by examiner

*Primary Examiner*—Michael Barr
(74) *Attorney, Agent, or Firm*—Oyen Wiggs Green & Mutala

(57) ABSTRACT

This invention relates to novel process of preparing chemically bonded composite hydroxide ceramics by exposing a thermally treated hydroxide ceramic to phosphate reagent and subsequent heat treating the resulting system to initiate a rapid chemical bonding reaction. Such combined hydroxide/chemical bonding process can be used to fabricate ceramics or ceramic coatings for a variety of high and low temperature applications, including corrosion protection, wear resistance, dielectric properties, metal reinforced ceramics, ceramic membranes, non-sticky surfaces, bio-active ceramics, thermal barrier ceramics, non-wetted surfaces, and others.

15 Claims, 8 Drawing Sheets

PROCESS FOR MAKING CHEMICALLY BONDED COMPOSITE HYDROXIDE CERAMICS

This application is a continuation-in-part of application Ser. No. 09/574,237, filed May 19, 2000.

FIELD OF THE INVENTION

This invention relates to a novel process of preparing chemically bonded composite hydroxide ceramics by exposing a thermally treated hydroxide ceramic to a phosphate reagent to produce a system and subsequently heat treating the system to initiate a rapid chemical bonding reaction.

BACKGROUND OF THE INVENTION

Chemical reactivity in systems containing phosphoric acid or various forms of phosphates have received attention in scientific and patent literature. Particularly, the refractory applications and dental cements applications of chemical bonding (CB) of ceramics through phosphating have been disclosed. (See D. Kingery, "Fundamental Study of Phosphate Bonding in Refractories, Part I,II,III", *J. Am. Cer. Soc.* 33 (1950) 239–50; J. Cassidy, "Phosphate Bonding Then and Now", *Am. Cer. Soc. Bull.* 56 (1977)640–43; J. Bothe and P. Brown, "Low Temperature Formation of Aluminum Orthophosphate", *J. Am. Cer. Soc.* 76 (1993) 362–68; and J. Bothe and P. Brown, "Reactivity of Alumina towards Phosphoric Acid", *J. Am. Cer. Soc.* 76 (1993) 2553–58.) For example, mixing aluminium oxide, or alumino-silicates, or zircon, or many other pure or mixed oxides (such as $Cr_2O_3$, $ZrO_2$ with phosphoric acid $H_3PO_4$ (PA) or monoaluminum phosphate $Al(H_2PO_4)_3$, (MAP) leads to reaction between the constituents and formation of chemical bond at relatively low temperatures of 200–400° C. These processes yield successful, commercial refractory materials. (See D. Kingery, "Fundamental Study of Phosphate Bonding in Refractories, Part I,II,III", *J. Am. Cer. Soc.* 33 (1950) 239–50.) The objective of these inventions was to produce monolithic ceramic while avoiding the usual high-temperature treatment (or "sintering") necessary to bond ceramic particles. Additionally, chemically bonded ceramics experience very small shrinkage processing, i.e. size and shape of the resulting chemically bonded component is approximately the same as those of the mixed and pressed powder component.

In another example of known prior art, zinc oxide mixed with zinc metal and aluminium hydroxide is further mixed with phosphoric acid. The mixture reacts and sets at room temperature yielding dental cement. The cementitious behaviour of phosphate-containing systems has been explored on a large scale if one of the oxides in the system exhibits substantial room temperature reactivity towards phosphates. For example, MgO rapidly reacts with monoaluminum phosphate to form hydrated magnesium phosphates that bond the aggregate components of the cold-setting concrete. Reaction bonding of alumina with phosphates has also been used to produce ceramics of controlled, fine pore structure such as molecular sieves U.S. Pat. No. 5,178,846. Phosphating of steel or aluminium produces a thin (1–10 $\mu$m) mildly protective layer which can be utilised as a bondcoat for subsequent application of organic paints, or other coatings, such as ceramic coatings.

In order to produce a phosphate-bonded ceramic, a chemical reaction is initiated between the phosphate-carrying reactant, for example orthophosphoric acid ($H_3PO_4$), and an oxide (such as alumina, zirconia, chromia, zinc oxide, and others). As a result, refractory phosphates, such as aluminium phosphate, are formed at relatively low temperatures. For example, for the system $Al_2O_3$—$H_3PO_4$—$Al(H_2PO_4)_3$, the reaction starts at 127° C., and is complete at about 500° C. At higher temperatures, the resulting amorphous aluminophosphates undergo a chain of crystallization-phase transformations, to eventually decompose to $P_2O_5$ and $Al_2O_3$ above 1760° C. (See Bothe and P. Brown, "Low Temperature Formation of Aluminum Orthophosphate", *J. Am. Cer. Soc.* 76 (1993) 362–68; and J. Bothe and P. Brown, "Reactivity of Alumina towards Phosphoric Acid", *J. Am. Cer. Soc.* 76 (1993) 2553–58.)

The systems of particular interest include ceramic particles that are chemically bonded to form a protective film on metallic substrate. The films can be used for surface modification in preparation for deposition of subsequent coatings (e.g. phosphate treatment of metals before painting) or for added protection against corrosion and/or wear. However, due to substantial reactivity of phosphates, e.g. phosphoric acid, towards metals, the systems involving metals (e.g. phosphate-containing coatings on metals, or coatings that contain metallic particles) must include means of controlling reactivity of such system. One of such systems disclosed in the scientific and patent literature, is a protective coating for metals (e.g. steel) that contains simultaneously phosphoric acid and aluminium metal particles. In such coating particulate aluminium is combined with the phosphoric acid solution, applied to surface of metal, and heat treated at 250–550° C. to bond the metal particles together, and to the substrate base metal. In such a coating formulation aluminium must be protected from extensive, and possibly violent, reaction with the phosphate. One of the best-known systems that achieve this objective has been disclosed in U.S. Pat. No. 3,248,251, where chromates or molybdates were added to the solution to effectively protect aluminium metal from excessive reaction with the phosphate. These predominantly metallic coatings are still widely applied to protect ferrous metals form corrosion and oxidation. Another similar system has been disclosed in U.S. Pat. No. 3,395,027. In an attempt to eliminate the use of environmentally dangerous chromates or molybdates, formulations rich in dissolved aluminium ions, e.g. less reactive towards aluminium metals, have been proposed by Stetson et al in U.S. Pat. Nos. 5,279,649 and 5,279,650. These formulations contained numerous other substances that were supposed to inhibit reactivity of phosphates towards aluminium particles. Yet another attempt to produce "environmentally friendly" phosphate bonding composition suitable for coatings is disclosed by Mosser et al in a series of U.S. Pat. Nos. 5,478,413; 5,652,064; 5,803,990 and 5,968,240. All of these formulations include complex mixtures of ions (in addition to the phosphate ion solution) with the objective to control reactivity of phosphates in coatings application. In one variant of such coating system, disclosed in U.S. Pat. No. 4,544,408, a water/acid dispersion premix of hydrated alumina (e.g. boehmite or pseudoboehmite) is admixed into the usual chromate/phosphate or molybdate/phosphate coating composition. The patent teaches that mixing the two solutions leads to gelation of the hydrated alumina particles and, as a result of this process, a thixotropic mixture is formed. The thixotropic nature of the mixture allows deposition of uniform coatings in the spin coating process. It is disclosed that particles of alumina or aluminium improve performance of such coatings. It is further claimed in U.S. Pat. No. 4,838,942 that the coating system containing aluminium particles and a mix of chromic, phosphorous, phosphoric acids and aluminium phosphate can be cured at very low temperature of 150° C. to 190° C.

Another area pertaining to the present invention includes fully ceramic systems (i.e. no metals are present) where very fine particles (nanometer size) of hydroxide ceramic (HC), such as boehmite AlOOH, are mixed with calcined ceramic, such as alpha aluminium oxide. (See S. Kwon and G. L. Messing, "Sintering of Mixtures of Seeded Bohemite and Ultrafine Alpha Alumina", *J. Am. Cer. Soc.* 83 (2000) 82–88; and M. Kumagai and G. L. Messing, "Controlled Transformation and Sintering of a Bohemite Sol-Gel by Alpha Alumina Seeding", *J. Am. Cer. Soc.* 68 (1985) 500–505.) These systems are referred to in the present invention as composite hydroxide ceramic CHC. During heat treatment the nanometer-size particles of HC decompose, releasing water, and form very active nanometer-size particles of aluminium oxide. In these systems the very large surface area (in excess of 100 m$^2$/gram), and thus high reactivity, of the thermally decomposed boehmite is utilised to accelerate sintering of the resulting aluminium oxide, i.e. full densification of such CHC is achieved at about 1300° C. The initially admixed particles of calcined alpha aluminium oxide act as nucleation site for alumina forming from thermally decomposing boehmite. These systems are useful in processing of dense alumina ceramics at relatively low temperatures, i.e. 1300° C. However, these temperatures are too high to be able to process ceramic coatings of CHC on most metals. Moreover, thermal decomposition of boehmite and consequent removal of water from such system leads to relative large shrinkage, in excess of 20%, of the resulting ceramic body. Thus the hypothetical CHC coating would crack during heat treatment, as the base metal would not experience any processing shrinkage. This shrinkage decreases if share of the calcined ceramic in the system increases. This phenomenon is well known in the prior art of ceramic processing, e.g. in refractory ceramic processing. For example, when compacting a refractory brick of ceramic powders that could substantially shrink upon heat treatment (e.g. clay components), a portion of previously fired and ground brick ("grog") is added to decrease the overall shrinkage, while maintaining chemical composition of the resulting brick essentially unchanged.

The same concept, as applied to ceramic coatings, has been introduced by Barrow et al. ("Thick Ceramic Coatings using a Sol Gel Based Ceramic—Ceramic 0–3 Composite:, *Surf. Coat. Tech.*, 76–77 (1995) 113) and disclosed in U.S. Pat. No. 5,585,136, re-issued as Re. No. 36,573. The authors teach that dispersion of up to 90% of fine calcined ceramic particles into sol-gel solutions allows depositing ceramic coatings and thick composite films on metals. The disclosed sol-gel solutions are obtained through relatively complex route of dissolving salts, organometalic compounds, such as alkoxides, or carboxylates and ketones. These systems, which can be classified as composite sol-gel (CSG), still need to be heat treated at relatively high temperature up to about 1000° C., to initiate ceramic bond formation.

A method to avoid these excessive temperatures and still achieve substantial ceramic bond in CSG has been recently disclosed by Troczynski and Yang, U.S. Pat. No. 6,284,682 B1, granted Sep. 4, 2001. In that invention, CSG ceramic coatings are subject to chemical bonding through phosphating reactions, i.e. by impregnation of CSG coatings with phosphoric acid H$_3$PO$_4$ (PA) or monoaluminum phosphate Al(H$_3$PO$_4$)$_3$, (MAP), or combination thereof. The high reactivity of the sol particles produced through dissolving salts, organometalic compounds, such as alkoxides, or carboxylates and ketones, allows rapid chemical bonding of CSG coatings at temperatures as low as 200° C. The chemically bonded composite sol-gel system is obtained (CB—CSG), useful for deposition of fully ceramic coatings on metals at low temperatures. Phosphating of aluminium salts has been used in the past (U.S. Pat. No. 4,927,673) for rapid hardening of molds for casting metals.

SUMMARY OF INVENTION

The present invention represents an inventive advance over the phosphate containing systems described above.

An objective of the present invention is to control reactivity of phosphates, such as phosphoric acid H$_3$PO$_4$ (PA), phosphorous acid H$_3$PO$_3$ (PA'), or monoaluminum phosphate Al(H$_3$PO$_4$)$_3$, (MAP), towards other components of the system (metallic or non-metallic), including molded ceramics and ceramic coatings, without any addition of secondary compounds such as molybdates or chromates. Such well-controlled phosphate systems allow, for example, deposition of environmentally clean ceramic coatings on metals or non-metals.

A further objective of this invention is to utilize the very high activity of thermally decomposed fine hydroxide ceramic, such as thermally dehydrated boehmite ceramic, to initiate chemical bonding through phosphating, and to control reactivity of the phosphates, such as phosphoric acid H$_3$PO$_4$ (PA), phosphorous acid H$_3$PO$_3$ (PA'), or monoaluminum phosphate Al(H$_3$PO$_4$)$_3$, (MAP), towards other components of the system (metallic and/or non-metallic).

A further objective of this invention is to use simple composite hydroxide ceramic (CHC) systems, such as boehmite ceramic mixed with calcined ceramic (for example alumina powder), to minimise shrinkage of the resulting ceramic coating, such that crack-free coatings are obtained.

A key feature of the subject invention is its ability to achieve high quality, dense ceramic coatings on metals and non-metals at low process temperatures, while avoiding complex ionic content, or complex sol-gel routes through dissolving salts, organometalic compounds, such as alkoxides, or carboxylates and ketones. The subject invention therefore discloses that suitable thermal treatment of the composite hydroxide ceramic (CHC), followed by chemical bonding (CB) through phosphating of CHC, can yield excellent, environmentally friendly chemically bonded composite hydroxide ceramics (CB—CHC). These materials are especially suitable as ceramic coatings.

One example of a procedure according to the invention is a mix of calcined alumina and hydroxide alumina (or hydrated alumina, such as boehmite) networks, which is heat treated at about 200° C. to de-hydrate the hydroxide and is then impregnated with a mix of metal phosphate and phosphorus acid. The phosphates and phosphorus acid react primarily with the active hydroxide derived alumina networks to form complex amorphous phosphates at about 300° C., which can crystallize upon heat treatment above about 600° C. The hydrated alumina derived alumina is subject to reaction with phosphoric acid to result in a polymerized network of monoaluminum phosphate. The phosphates also partially react with calcined alumina, thereby providing a strong bond between the alumina filler particles, and the continuous matrix phosphate phase. In order to achieve the desired properties, the kinetics of the phosphating reaction must be controlled to prevent substantial reaction of the phosphate with the substrate, which is undesirable because it can lead to reaction product buildup at the interface and spallation of the coating. The kinetic reaction control is achieved through the use of an active hydroxide-derived phase (e.g. through dehydration of boehmite) with an inert ceramic filler, and phosphate phase, in proper ratio, particle size, and concentration across the coating.

The invention is directed to a process of preparing a chemically bonded ceramic comprising phosphating a hydroxide derived oxide or hydrated oxide ceramic with heat treatment at a temperature between about 200° C. and about 1200° C.

The hydroxide derived oxide can be a first phase and can be impregnated with a secondary phosphate phase which can react with the oxide ceramic first phase. In one embodiment of the invention, a mixture of calcined alumina and hydroxide alumina, such as boehmite (AlOOH), can be heat treated in air at about 200° C. to 300° C. to decompose the hydroxide alumina, and then impregnated with a mixture of metal phosphate and phosphorus acid to form complex amorphous phosphates which can crystallize under further heat treatment. In another embodiment of the invention, porosity in the surface of the ceramic coating can be sealed by utilizing a process selected from the group consisting of hydroxide impregnation, hydroxide electrophoretic deposition, aluminum phosphate impregnation, phosphorus acid impregnation, or a combination of these treatments.

In a specific embodiment, the invention involves a process of preparing a chemically bonded ceramic comprising: (a) as a first step, preparing a slurry of solvent and hydroxide ceramic: (b) as a second step, heat treating the hydroxide ceramic slurry at a temperature of between about 100 to 800° C. to produce a dehydrated oxide ceramic: (c) as a third step, impregnating the dehydrated oxide ceramic with a phosphating agent; and (d) as a forth step, heat treating the phosphate impregnated oxide ceramic at a temperature between 200° C. and 1200° C. to seal pores in the ceramic and produce a phosphated oxide ceramic powder to produce a mixed slurry; (b) applying said mixed slurry to a substrate to thereby coat the substrate with the ceramic hydroxide slurry; (c) heating the ceramic hydroxide coated substrate at a temperature up to about 300° C. to 1000° C. to produce a ceramic metal oxide film on the substrate; and (d) sealing surface pores of the ceramic coating with a phosphorus containing ceramic sealant.

The hydrated ceramic oxide can be one or more of $SiO_2$, $Al_2O_3$, $ZrO_2$, $TiO_2$, BeO, SrO, BaO, CoO, NiO, ZnO, PbO, CaO, MgO, $CeO_2$, $Cr_2O_3$, $Fe_2O_3$, $Y_2O_3$, $Sc_2O_3$, $HfO_2$ or $La_2O_3$. The phosphating agent can be a metal phosphate, phosphoric acid, or mixtures thereof. The metal in the phosphate can be one or more of Al, Zr, Ti, Mg, Cu, Fe, Ca, Sr, Hf or Cr. The process can include a calcined ceramic filler comprised of powders or fibers of oxides, carbides, nitrides, borides, fluorides, suphides or mixtures thereof.

The invention is also directed to a process of preparing a chemically bonded hydroxide ceramic coating deposited on a substrate comprising phosphating a hydroxide derived oxide ceramic deposited on the substrate for sufficient time to seal pores in the ceramic, but for insufficient time to attack the substrate, and polymerizing the resulting product with heat treatment at a temperature between about 200° C. and about 1200° C.

The invention also pertains to a method of preparing a ceramic hydroxide coating on a substrate which comprises: (a) immersing a substrate coated with a ceramic hydroxide coating into a solution containing dispersed boehmite; (b) withdrawing the ceramic hydroxide coated substrate from the boehmite alumina solution and drying the coated substrate at a temperature of about 100° C.; (c) heat treating the dried coated substrate at a temperature of about 200° C. for about 10 min. to substantially dehydrate the boehmite; (d) applying a phosphoric acid solution on the surface of the ceramic coated substrate to seal the pores in the ceramic coating for sufficient time that permits the alumina resulting from dehydration of boehmite to react with the phosphoric acid solution sufficiently rapidly to seal pores in the alumina ceramic coating, but for insufficient time that the underlying substrate is exposed to substantial phosphating reaction. The phosphoric acid can be reacted with the dehydrated boehmite coating at about 300° C. for about 10 minutes. The reaction of the phosphoric acid with the dehydrated boehmite ceramic coating can yield a polymerized network of mono-aluminum phosphate within and on the surface of the coating.

The invention is also directed to a method of preparing an alumina/alumina composite hydroxide ceramic (CHC) coating on a substrate which comprises mixing boehmite and calcined aluminium oxide in water at a pH of 2 to 6 to produce a suspension, agitating the suspension to produce a homogenous slurry, immersing a Substrate in the slurry to coat the substrate, and drying the composite hydroxide ceramic coating at a temperature of 50 to 200° C. Other ceramic particles, such as zirconia particles can be substituted for the calcined aluminum oxide. The porous coating resulting from this process is then sealed using chemical bonding process through phosphating, as described above. Alternatively, the solvent can be methyl alcohol, ethyl alcohol or isopropyl alcohol.

The invention also pertains to a method of sealing porosity of ceramic coatings comprising impregnating the porous ceramic coating with mono-aluminum phosphate for about 10 to 50 min., and heating the impregnated coatings at a temperature of about 300° C. for about 20 to 50 min. The product may be further heat treated at temperatures of 500 to 800° C. for about 10 to 50 min to crystallize the polymerized complex glassy phosphases resulting from the reaction.

The invention also includes a method of sealing a composite hydroxide ceramic coating on a substrate with phosphoric acid which comprises treating the coating with phosphoric acid for about 1 to 20 min., and polymerising the resulting product at a temperature of about 300° C. for 20 to 50 min.

The invention is also directed to a process for producing a porosity sealed ceramic film on a substrate comprising: (a) mixing a hydroxide solution with a metal oxide ceramic powder to produce a mixed slurry; (b) applying said mixed slurry to a substrate to thereby coat the substrate with the ceramic hydroxide slurry; (c) heating the ceramic hydroxide coated substrate at a temperature up to about 600° C. to 1000° C. to produce a ceramic metal oxide film on the substrate; and (d) sealing surface pores of the ceramic coating with a phosphorus containing ceramic sealant.

The ceramic sealing process can be selected from the group of processes comprising hydroxide impregnation, hydroxide electrophoretic deposition, aluminum phosphate impregnation or phosphorus acid impregnation.

BRIEF DESCRIPTION OF DRAWINGS

In drawings which illustrate specific embodiments of the invention, but which should not be construed as restricting the spirit or scope of the invention in any way.

FIG. 1 is a CB—CHC coating on stainless steel substrate. An approximately 96% dense, 60 µm thick film is shown.

FIG. 2 presents similar, but only 25 µm thick, CB—CHC coating on copper substrate.

FIG. 3 shows 30 μm thick CB—CHC coating on carbon fiber reinforced epoxy composite.

FIG. 4 illustrates 30 μm thick CB—CHC SiC—Al$_2$O$_3$ coating on aluminum alloy substrate.

FIG. 5 presents 170 μm thick CB—CHC thermal barrier coating on nickel alloy substrate, with enlarged grain size and porosity.

FIG. 6 is 40 μm thick CB—CHC coating on magnesium alloy substrate.

FIG. 7 is a CB—CHC membrane, showing coarse (top) and fine (5 μm thick bottom) porosity films.

FIG. 8 presents microstructure of the coarse porosity film of CB—CHC membrane.

DETAILED DESCRIPTION OF SPECIFIC EMBODIMENTS OF THE INVENTION

General Principles and Characteristics

Figure 1:
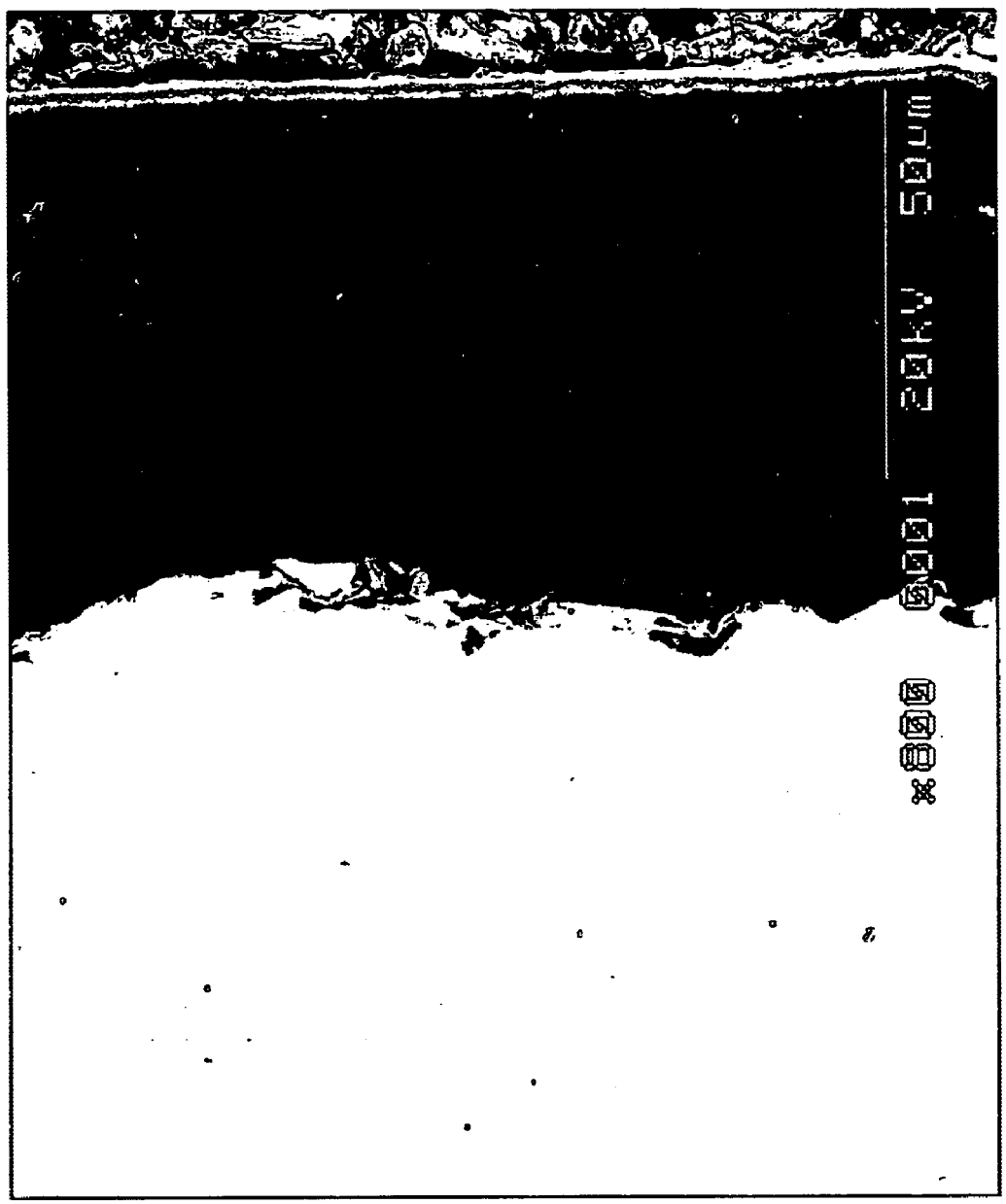
FIGS. 1 to 8 illustrate SEM microstructures of several alumina/alumina CB—CHC (Chemically Bonded Composite Hydroxide Ceramic) coating, deposited on a variety of substrates.

A new, generic method for deposition of low porosity ceramic coatings of Chemically Bonded Composite Hydroxide Ceramic (CB—CHC) is disclosed. CB—CHC is a novel process which comprises an inventive combination of dispersable, fine hydroxide technology, Composite Hydroxide Ceramic (CHC) technology, and the reactivity between phosphates and metal oxides or hydroxides.

The key discovery of the subject invention is that the hydrated ceramic oxide after calcination at mild temperature of 100° C. to 1000° C., preferably about 200° C. to 300° C., reacts rapidly with the phosphates and/or phosphoric acid and thus forms an excellent ceramic binder for other ceramic or metallic particles (fillers) present in the system. In applying the invention to the processing of ceramic coatings, the reaction is sufficiently rapid that the underlying metallic substrate is not exposed to damaging phosphating reactions. By using the above processes of the invention, non-permeable and crack-free thick ceramic coatings (from few μm, and up to several mm thick) have been successfully fabricated on variety of substrates including steel, Ti, Cu, Al, Mg, fiber reinforced epoxy, ceramic, in simple spray painting/curing operation. The resulting coatings had bonding strength generally above 45 MPa, and surface hardness generally above 7 GPa. The ceramic coatings produced according to the subject invention can be used to produce incremental wear and corrosion protection; dielectric coatings; thermal barrier coatings; bioactive coatings and also for sealing porous ceramic coatings and bulk materials, for improved corrosion and wear resistance. In another variant of the invention, high fraction of porosity may be allowed in thicker CB-CHC films to achieve low thermal conductivity (e.g. for thermal barrier coatings applications) or to achieve permeable membrane, useful for filtration of liquids or gases.

In this application, the inventors disclose that chemical bonding through phosphating of hydroxide derived oxides leads to dense, hard, wear and corrosion resistant ceramics for variety of applications, including coatings and bulk components. In the case of coatings, the bonding is achieved after heat treatment at temperatures as low as 300° C., without chemically attacking the substrate by the phosphates. The key phenomenon of the disclosed process is the reactivity of the fine particles resulting from thermal decomposition of hydroxide ceramic, with phosphate precursors. The inorganic products of this reaction polymerize and form complex phosphates, which may crystallize at elevated temperatures. Such combined hydroxide/oxide/chemical bonding process can be used to fabricate dense, thick, low permeability ceramics or ceramic coatings at relatively low temperatures, for a variety of applications, including providing high temperature corrosion protection, wear resistance, dielectric properties, non-sticky surfaces, non-wetted surfaces, thermal barrier ceramics, bio-active ceramics, and others.

In a specific embodiment, the invention involves a process of preparing a chemically bonded ceramic comprising: (a) as a first step, preparing a slurry of solvent and hydroxide ceramic; (b) as a second step, heat treating the hydroxide ceramic slurry at a temperature of between 100° C. to 800° C. produce a dehydrated oxide ceramic; (c) as a third step, impregnating the dehydrated oxide ceramic with a phosphating agent; and (d) as a fourth step, heat treating the phosphate impregnated oxide ceramic at a temperature between about 200° C. and about 200° C. to seal pores in the ceramic and produce a phosphated oxide ceramic temperature of the ceramics. The problems limiting the applications of conventional ceramic processing for coating technology for corrosion and wear protection include cracking due to significant shrinkage. This problem has recently been partially addressed in the application of modified sol-gel technology for deposition of thick ceramic coatings (U.S. Pat. No. 5,585,136, Barrow et al. Queens University). Thicker coatings (up to 6 μm in single deposition and up to 200 μm in multiple depositions) evidently did not crack upon drying because the gel phase contained up to about 90% wt. of the filler calcined (i.e. not shrinking upon heat treatment) ceramic. These coatings were however produced through complex sol-gel routes dissolving salts, organometallic compounds, such as alkoxides, or carboxylates and ketones. The authors disclose in S. Kwon et al., Sintering of Mixtures of Seeded Bohemite and Ultrafine Alpha Alumina", *J. Am. Cer. Soc.* 83 (2000) 82–88, and M. Kumagi et al., "Controlled Transformation and Sintering of a Bohemite Sol-Gel by Alpha Alumina Seeding", *J. Am. Cer. Soc.* 68 (1985) 500–505, a process where the stable dispersion of calcined ceramic in a sol is applied to a substrate, without a substantial temperature differential therebetween, so as to provide a coating thereon up to about 6 μm thick. The resulting coating is subsequently fired so as to remove the organic constituents related to sol-gel processing. Even though active sol particles allow decrease of heat treatment temperature for the coatings disclosed in above mentioned U.S. Pat. No. 5,585,136, weak bonding persists between coating and substrate, and permeability of the ceramic structure to gases and liquids persists (if porous). That is, even when the coatings were heat treated at temperatures up to 1000° C., residual porosity persists, thereby giving relatively low hardness for the coating and a high permeability to gases and liquids. The high temperature requirement for heat treatment is unacceptable for most metallic substrates due to melting (e.g. Al, Mg, Pb, Zn and others), or oxidation if heat treated in air, or microstructural deterioration. It has been disclosed in the recent U.S. Pat. No. 6,284,682 B1 that this particular porosity and hardness problem can be addressed through use of a phosphate ceramic sealant by any of a number of techniques including impregnation, electrophoretic deposition, aluminum phosphate impregnation, phosphorus acid impregnation, and/or combinations of these treatments.

In this invention, hydrated ceramic oxides suspended in water/acid mixture are utilised as a dispersing medium for calcined ceramic filler material, and as reactants providing chemical bonding to the resulting ceramic body, e.g. coating. The hydrated ceramic oxides include one or more SiO$_2$, Al$_2$O$_3$, ZrO$_2$, TiO$_2$, BeO, SrO, BaO, CoO, NiO, ZnO, PbO, CaO, MgO, CeO$_2$, Cr$_2$O$_3$, Fe$_2$O$_3$, Y$_2$O$_3$, Sc$_2$O$_3$, HfO$_2$ or La$_2$O$_3$. The chemical bonding agent include metal phosphates, phosphoric acid, or mixtures or suspensions of same in liquid media, such as water or organic liquids. The metal in the phosphates includes one or more of Al, Zr, Ti, Mg, Cu, Fe, Ca, Sr, Hf, Cr, Ba, Mo, Ni, Zn, Pb, Sn. The calcined ceramic filler material may include essentially any ceramic in any form, i.e. powders or fibers of oxides, carbides, nitrides, borides, fluorides, sulphides or mixtures thereof. Metallic particles may be also added to this system.

Composite Hydroxide Ceramic (CHC) processing offers many advantages over conventional ceramic processing, including high purity, homogeneity, and low sintering temperature of the ceramics. The problems limiting the applications of CHC for coating technology for corrosion and wear protection include cracking due to significant shrinkage. This problem has recently been partially addressed in the application of modified sol-gel technology for deposition of thick ceramic coatings (U.S. Pat. No. 5,585,136, Barrow et al., Queens University). Thicker coatings (up to 6 $\mu$m in single deposition and up to 200 $\mu$m in multiple depositions) evidently did not crack upon drying because the gel phase contained up to about 90% wt. of the filler calcined (i.e. not shrinking upon heat treatment) ceramic. These coatings were however produced through complex sol-gel routes through dissolving salts, organometalic compounds, such as alkoxides, or carboxylates and ketones. The authors disclose in S. Kwon et al., Sintering of Mixtures of Seeded Bohemite and Ultrafine Alpha Alumina", *J. Am. Cer. Soc.* 83 (2000) 82–88, and M. Kumagi et al., "Controlled Transformation and Sintering of a Bohemite Sol-Gel by Alpha Alumina Seeding", *J. Am. Cer. Soc.* 68 (1985) 500–505, a process where the stable dispersion of calcined ceramic in a sol is applied to a substrate, without a substantial temperature differential therebetween, so as to provide a coating thereon up to about 6 $\mu$m thick. The resulting coating is subsequently fired so as to remove the organic constituents related to sol-gel processing. Even though active sol particles allow decrease of heat treatment temperature for the coatings disclosed in above mentioned U.S. Pat. No. 5,585,136, weak bonding persists between coating and substrate, and permeability of the ceramic structure to gases and liquids persists (if porous). That is, even when the coatings were heat treated at temperatures up to 1000° C., residual porosity persists, thereby giving relatively low hardness for the coating and a high permeability to gases and liquids. The high temperature requirement for heat treatment is unacceptable for most metallic substrates due to melting (e.g. Al, Mg, Pb, Zn and others), or oxidation if heat treated in air, or microstructural deterioration. It has been disclosed in the recent U.S. Pat. No. 6,284,682 B1 that this particular porosity and hardness problem can be addressed through use of a phosphate ceramic sealant by any of a number of techniques including impregnation, electrophoretic deposition, aluminum phosphate impregnation, phosphorus acid impregnation, and/or combinations of these treatments.

In order to overcome the high shrinkage problem of hydroxide processing, calcined ceramic powders or fibers (ceramic fillers) may be mixed with hydroxide and water to fabricate high performance composite hydroxide ceramics. The shrinkage of these bodies decreases because of the presence therein of the significant amount of inert ceramic powders or fibers. The additional advantages of hydroxide processing for ceramic composites are fine scale mixing and low densification temperature, leading ultimately to improved properties. This composite hydroxide technology can be used to fabricate crack-free thick ceramic coatings, up to several hundred $\mu$m thick, on metallic or nonmetallic substrates. Prior art knowledge shows, however, that these composite hydroxide coatings cannot be densified and gain enough strength and hardness if cured below about 1000° C. For most metallic substrates of interest, however, including aluminum and magnesium alloys, the maximum curing temperature must be below about 600° C. The subject invention solves this dilemma because it allows production of chemically-bonded, dense and hard composite hydroxide coatings on substrates or bulk ceramic components in this temperature range.

The currently disclosed invention teaches that fine hydroxide ceramics (such as aluminum hydroxide AlOOH, also known as aluminum oxide monohydrate or bohemite, or zirconium hydroxide Zr(OH)$_4$) can be utilized as an active ingredient of compositions suitable for deposition of environmentally friendly ceramic coatings. The active oxide ceramic, resulting from heat treatment of the fine hydroxides at 200–300° C., rapidly reacts at relatively low temperatures with phosphate, such as orthophosphoric acid or aluminum phosphate, to form a ceramic binder. This binder can be used by itself to produce chemically bonded ceramic coatings or bulk components. The binder can also be used to bond secondary materials, such as ceramics or metals, to produce chemically bonded composite ceramic coatings or bulk components. Once chemically bonded at low temperature (200–300° C.), the bond maintains high strength to very high temperatures, up to about 1500° C. The present invention does not use organometallics nor salts as the starting raw materials. The starting raw materials are hydroxides (i.e. hydrated oxides, such as boehmite AlOOH), which may or may not be accompanied by secondary calcined ceramic particles, and are subsequently heat treated and then chemically bonded, using for example phosphates. The method does not use organic liquids, organometallics or any salts as precursors for the coating composition. The only components of the coating systems, as disclosed below in detailed description, include water (adjusted to acidic pH=2 to 6 using e.g. nitric acid), the hydroxide ceramic (e.g. boehmite), the inert calcined ceramic filler (e.g. calcined alpha alumina). Such coating system is deposited on metal substrate using any means of spraying, dip-coating, spin-coating, electrophoretic coating, and others. The deposited coating is heated at 100–800° C. to dehydrate the fine hydroxide ceramic in preparation for the subsequent chemical bonding through phosphating step. There is no organic constituents released upon heat treatment of the coating (only water is being released). After the dehydration heat treatment, the chemical bonding process is initiated by providing contact between the fine oxide ceramic particles resulting from decomposition of hydroxide ceramic, and the phosphate reactants, such as phosphoric acid or monoaluminum phosphate. This is accomplished by using any means of spraying, dip-coating, spin-coating, electrophoretic coating, and others. Elevating system temperature to approximately 100–1000° C. completes the chemical bonding reaction between the phosphate reactant and oxide components of the coatings.

It is further disclosed that the coating system described above can be applied to a substrate remaining at a wide ranges of temperatures, approximately from 0° C. to 1000° C. The coating can be also applied in wide range of thickness increments, from about 10 $\mu$m to about 2 mm. A wide range of geometry and shapes can be coated, including out-of-sight geometry and concave shapes. This is particularly suitable for coating internal surfaces of pipes and pipelines. The process is environmentally benign and non-invasive towards metals. It is exclusively water-based processing, i.e.

there are no organic constituents to be removed from solvents during processing. The principal components are known to be environmentally friendly, e.g. alumina and aluminum hydroxide powders are components of toothpaste, and phosphates are components of human bone.

Whereas the key, well defined characteristic of the disclosed process is the rapid/low temperature reaction between the calcined hydroxide ceramic (such as boehmite) and the phosphate reactant (i.e. phosphoric acid or metal phosphate), the chemical nature, morphology, or presence/absence of the additional filler phases can be variable. Although the above presentation focused on applications were wear and corrosion protection may be sought (hence use of hard/inert alpha alumina powder filler), many alternate fillers and applications are envisioned. For example, the very same system containing calcined boehmite/phosphate/alpha alumina has been determined as an excellent dielectric film for insulation of both low voltages (e.g. in thermoelectric generators) and high voltages (e.g. in high power electric circuits). Many other ceramics may replace alumina for wear/corrosion/dielectric applications, as most ceramics are wear and corrosion resistant and are also electrical insulators. Another application involves active filler particles, e.g. magnetic material particles or material piezoelectric particles. In application to bio-active ceramics, the filler may be a hydroxyapatite or other calcium phosphate ceramic. Solid lubricants, such as BN or MoS2 can be used as a filler to modify (decrease) friction coefficient between coated components. High-temperature polymer particles that can survive the 300° C. heat treatment temperature for chemical bonding, e.g. PTFE, can also be used as a secondary filler phase. The metallic filler phases in the form of particles or fibers may be used to increase fracture toughness of the coatings.

EXAMPLES

General Example 1
Processing of Chemically Bonded Hydroxide Ceramic

The coating slurry was prepared by mixing 200 g of aluminum hydroxide powder (boehmite AlOOH, equivalent to aluminum oxide monohydrate $Al_2O_3 \cdot H_2O$) and 750 g of alpha alumina powder (average particle size about 0.5 µm), in 1 liter of distilled water. The slurry acidity and viscosity was adjusted to approximately pH=4 using 1 M nitric acid. At this stage the slurry viscosity was approximately 20 mPa.s. The slurry was deposited on a substrate at room temperature by spray-coating, dip-coating, spin-coating, and electrophoretic deposition. The coating thickness varied between approximately 10 µm and 3000 µm, depending on the method of deposition. The coatings were subsequently dried in air at room temperature for about 1 hr (thinner coatings) and 4 hrs (thicker coatings) and then calcined at 250° C. for 20 min, then cooled to room temperature. The heat treatment can be performed in an oven, or equally well through application of surface flame or a radiant source. At this stage, a 35% 45% porous coating is obtained, in which the alpha alumina particles are bonded with the very fine (approximately 10–30 nm) amorphous alumina particles resulting from dehydration of the fine hydroxide (boehmite) particles. Further elimination of porosity of such system to below 5% would normally require heat treatment above 1200° C., excluding application to most metals in air. However, chemical bonding through phosphating according to the subject invention enables a reduction of the total porosity to less than 3% (open porosity near zero), at temperatures 200° C. to 600° C.

The small size of the oxide particles produced from the hydrated oxide is critical to provide sufficient reactivity in the presence of chemical bonding agent, e.g. phosphate or phosphoric acid. Dispersing ceramic powders or fibers (of oxides, carbides, nitrides, fluorides, or others) into the initial slurry forms the composite hydroxide ceramics (CHC). If such calcined ceramic powder particles are dispersed in the slurry, a dramatic decrease of densification strain results, thereby allowing processing of ceramic coatings and bulk shapes of unlimited size and shape. Simultaneously, the nature of the dispersed phase may be varied independently of the type of the bonding phase, thereby providing a high degree of flexibility in the custom design of ceramics for any given application. However, such ceramics must be further heat treated at relatively high temperatures, i.e. above 1200° C., in order to form ceramic bond and eliminate porosity.

In order to achieve substantially full densification of the body at a temperature below 600° C., an add-on chemical bonding process, according to the invention, is required. In one example of the invention, the monoaluminum phosphate (MAP), $Al(H_2PO_4)_3$, derived from $Al_2O_3$—$H_3PO_4$—$H_2O$ system, is used along with $H_3PO_4$ to initiate and control the phosphating reactions with the fine oxide particles derived by dehydration of the fine hydroxide particles (boehmite). The following reactions are initiated between hydroxide-derived alumina, calcined alumina and the phosphates:

$$Al_2O_3 + 6H_3PO_4 \rightarrow 2Al(H_2PO_4)_3 + H_2O$$

$$Al(H_2PO_4)_3 \leftarrow \rightarrow 2H_3PO_4 | AlPO_4 x H_2O$$

Formation of hydrated aluminum phosphates occurs if excess alumina is present, since $Al(H_2PO_4)_3$ is still capable of reacting, according to the reaction:

$$Al(H_2PO_4)_2 + Al_2O_3 \, _z 900 \; 3AlPO_4 + 3H_2O$$

The reaction of orthophosphoric acid with aluminum oxide yields several different products depending on the type of alumina, the composition, reaction time and temperature. The combined effects of very high specific surface area and alumina concentration determine the kind and relative amounts of phosphates obtained by the action at a fixed temperature and time. The preferred system involves reaction of the alumina clusters with well adhering, 10–3000 µm thick films for structural or functional applications. Deposition of thick, dense, fully ceramic films is accomplished in a simple painting-low temperature curing operation. Typical microstructure of the resulting coating is illustrated in FIG. 1.

The described above general example is further illustrated through the following flowsheet:

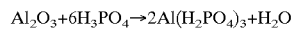
Schematic Flowsheet of Process for Producing
Low Porosity Alumina Ceramic Coatings on Stainless Steel
by Chemical Bonding of Composite Boehmite

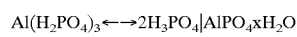
Mix 200 g boehmite 750 g calcined alumina in water
Adjust pH to 4

↓

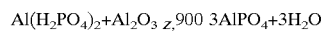
Composite Hydroxide Ceramic slurry (CHC) ready for coating

↓

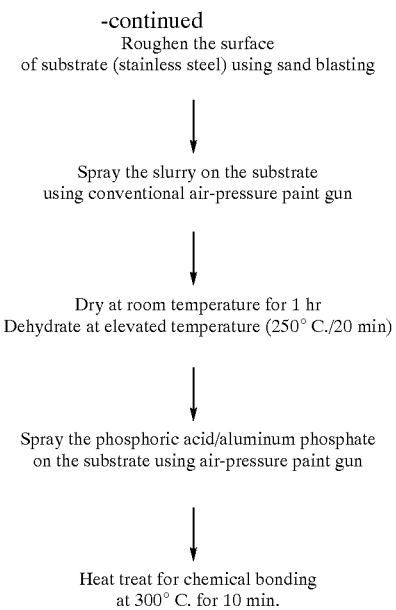

Roughen the surface of substrate (stainless steel) using sand blasting

↓

Spray the slurry on the substrate using conventional air-pressure paint gun

↓

Dry at room temperature for 1 hr
Dehydrate at elevated temperature (250° C./20 min)

↓

Spray the phosphoric acid/aluminum phosphate on the substrate using air-pressure paint gun

↓

Heat treat for chemical bonding at 300° C. for 10 min.

Example 2
Chemically Bonded Hydroxide Ceramic Coatings Deposited on Cold Stainless Steel Substrates The coating slurry was prepared by mixing 200 g of aluminum hydroxide powder (boehmite) and 750 g of alpha alumina powder (average particle size about 0.5 μm), in 1 liter of distilled water. The slurry acidity and viscosity was adjusted to approximately pH=4 using 1 M nitric acid. At this stage the slurry viscosity was approximately 20 mPa.s. The slurry was deposited on stainless steel solid substrate at room temperature by spray-coating, dip-coating, spin-coating, and electrophoretic deposition. The coating thickness varied between approximately 5 μm and 1000 μm, depending on the method of deposition. The coatings were subsequently dried in air at room temperature and then calcined at 250° C. for 10 min, then cooled to room temperature. Subsequently the resulting porous coatings were infiltrated by 50% phosphoric acid and reheated to 300° C. for 10 min. The resulting coatings had low porosity (approximately 6% pores by volume), high bonding strength (48 MPa), and high surface hardness (7.2 GPa). The resulting coatings were suitable for enhanced wear/corrosion protection of the metal surface. If the last step of infiltration by 50% phosphoric acid and reheating to 300° C. for 10 min was repeated three times, the resulting coatings had decreased porosity (approximately 3% pores by volume), increased bonding strength (50 MPa), and increased surface hardness (7.9 GPa).

Example 3
Chemically Bonded Hydroxide Thick Ceramic Coatings Deposited on Hot Stainless Steel Substrates The coating slurry was prepared by mixing the powders of 150 g aluminum hydroxide (boehmite), 500 g zirconia (average particle size about 1.5 μm), and 300 g alumina (average particle size about 0.5 μm), in 1 liter of distilled water. The slurry acidity and viscosity was adjusted to approximately pH=4 using 1 M nitric acid. At this stage the slurry viscosity was approximately 20 mPa.s. The slurry was deposited on stainless steel solid substrate at 300° C. by spray-coating, and the substrate temperature was maintained for 10 minutes after deposition, then cooled to room temperature. Subsequently the resulting thick (0.1–5 mm) porous coatings were infiltrated by 50% phosphoric acid and reheated to 300° C. for 10 min. The resulting coatings were suitable for thermal barrier coatings (TBC) and die coating for metal casting. The resulting coatings had high thermal shock resistance and thermal cycling resistance.

Example 4
Chemically Bonded Hydroxide Ceramic Coatings Deposited on Low-Carbon Steel Substrates The coating slurry was prepared as in the above example 1. The slurry was deposited on low-carbon steel substrates at room temperature by spray-coating. The coating thickness varied between approximately 50 μm and 60 μm. The coatings were subsequently heat treated and chemically bonded as in the above example 1. The resulting coatings had low porosity (approximately 6% pores by volume), high bonding strength (49 MPa), and high surface hardness (7.0 GPa). The resulting coatings were suitable for enhanced corrosion protection of the metal surface in molten zinc and molten aluminum environment. Additionally, it was found that the resulting coatings were suitable for enhanced corrosion protection of marine structures in simultaneous presence of salt, marine organisms attaching to component surface, and sand abrasion.

Figure 4:

Example 5
Chemically Bonded Hydroxide Ceramic Coatings Deposited on Aluminum Alloy Substrates The coating slurry was prepared by mixing 150 g of aluminum hydroxide powder (boehmite) and 700 g of alpha alumina powder (average particle size about 0.5 μm), in 1 liter of distilled water. The slurry acidity and viscosity was adjusted to approximately pH=4 using 1 M nitric acid. At this stage the slurry viscosity was approximately 20 mPa.s. The surface of 6061 aluminum alloy substrate was treated with 30% phosphoric acid to form 0.2 μm thick interlayer phosphate coatings, followed by heat-treating at 300° C. for 10 min. The final coating slurry was deposited on 6061 aluminum alloy substrate at room temperature by spray-coating or dip-coating, to thickness of approximately 50 μm. The coatings were subsequently dried in air at room temperature and then calcined at 250° C. for 10 min, then cooled to room temperature. Subsequently the resulting porous coatings were infiltrated by 20% monoaluminum phosphate and reheated to 300° C. for 10 min. The last step of chemical bonding process was repeated two more times. The resulting coatings had low porosity (approximately 3% pores by volume), high bonding strength (40 MPa), and high surface hardness (6.8 GPa). The resulting coatings were suitable for enhanced wear/corrosion protection of the surface of aluminum alloy. Applications involving aluminum heat exchangers and oil pumps were targeted. Additionally, it was found that the resulting coatings were suitable for dielectric films for thermoelectric generators made of aluminum alloy. If part of the alpha alumina filler powder is replaced with SiC, enhanced thermal conductivity and wear resistance of the coating results. Typical microstructure of such coating is illustrated in FIG. 4.

Figure 6:
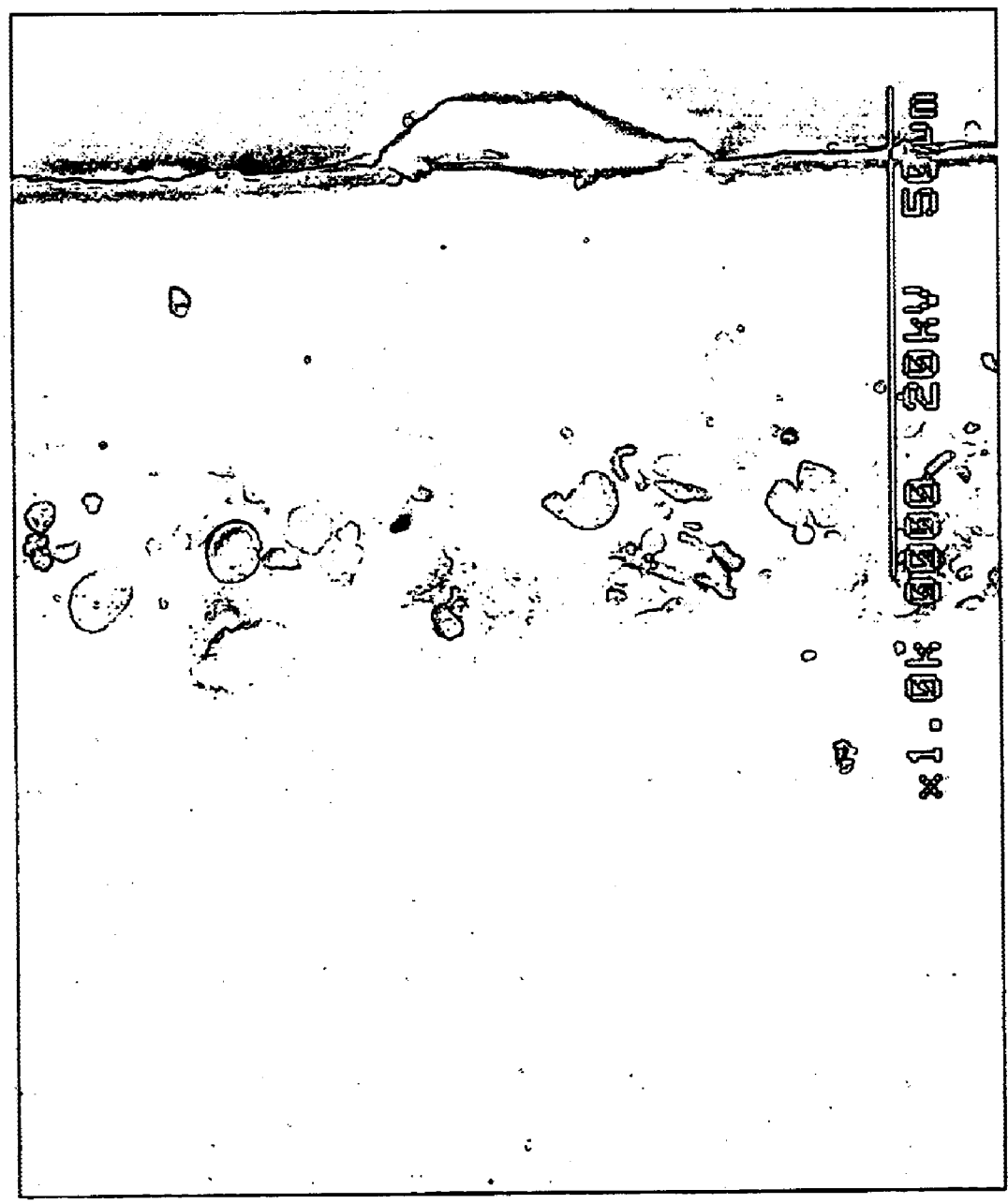

Example 6
Chemically Bonded Hydroxide Ceramic Coatings Deposited on Magnesium Alloy Substrates The coating slurry and surface of AZ91D magnesium alloy were prepared as in the above example 5. Similarly, the coating slurry was deposited and heat treated as in the above example 5. The chemical bonding process used highly diluted monoaluminum phosphate due to the high reactivity of the substrate. The porous coatings were infiltrated by 15% monoaluminum phosphate and heated to 300° C. for 10 min. The last step of chemical bonding process was repeated two more times. The resulting coatings had low porosity (approximately 3% pores by volume), high bonding strength (41 MPa), and high surface hardness (6.1 GPa). The resulting coatings were suitable for enhanced wear/corrosion protection of the surface of magnesium alloy. Typical microstructure of the resulting coating is illustrated in FIG. 6.

Example 7
Chemically Bonded Hydroxide Ceramic Coatings Reinforced with Metallic Particles The coating slurry was prepared by mixing 200 g of aluminum hydroxide powder (boehmite), 500 g of alpha alumina powder (average particle size about 0.5 μm), and 250 g aluminum powder (average particle size about 40 μm) in 1 liter of distilled water. The slurry acidity and viscosity was adjusted to approximately pH=4 using 1 M nitric acid. At this stage the slurry viscosity was approximately 20 mPa.s. The slurry was deposited on aluminum alloy at room temperature by spray-coating, dip-coating, and spin-coating deposition. The coating thickness was approximately 100 μm. The coatings were subsequently dried in air at room temperature and then calcined at 250° C. for 10 min, then cooled to room temperature. Subsequently the resulting porous coatings were infiltrated by 20% monoaluminum phosphate and reheated to 300° C. for 10 min. The resulting coatings had low porosity (approximately 7% pores by volume) and high bonding strength (41 MPa). The resulting coatings were suitable for enhanced wear/corrosion protection of the metal surface, in presence of thermal and/or mechanical strain cycling.

Figure 7:
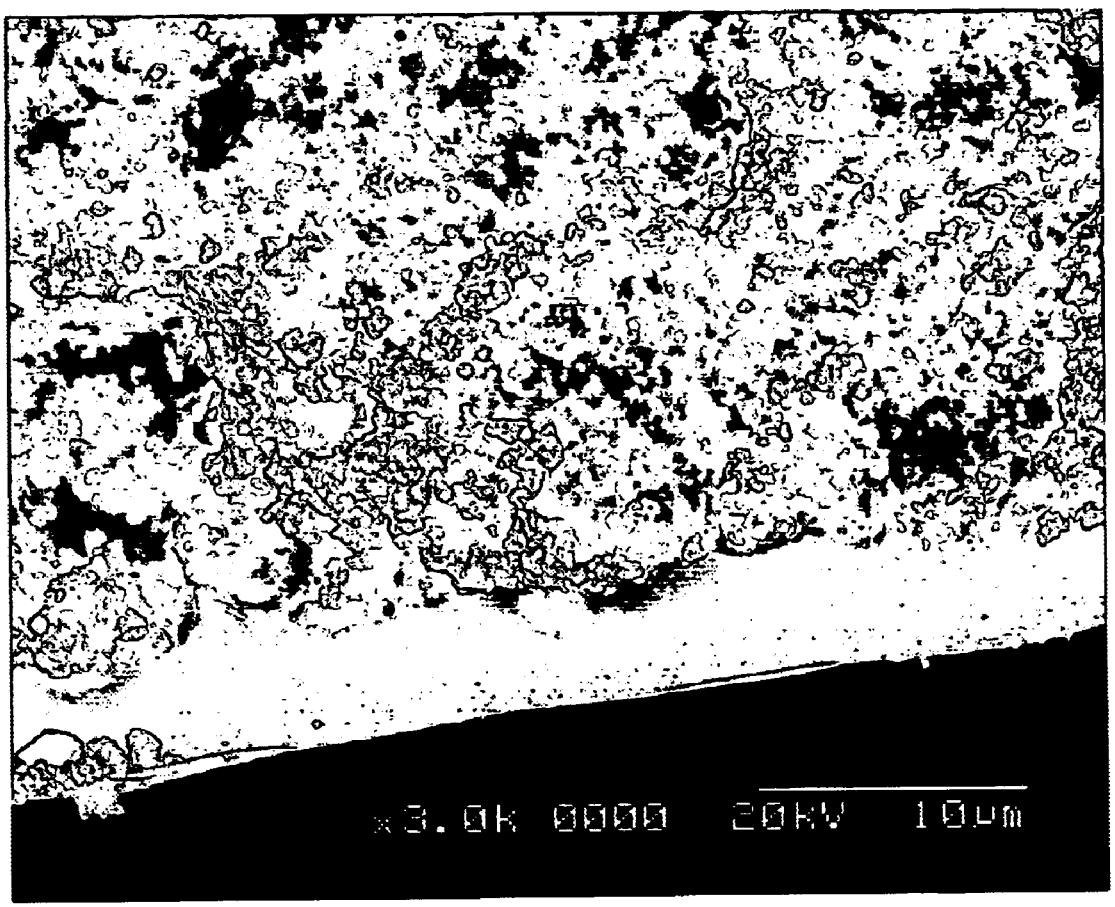
Figure 8:
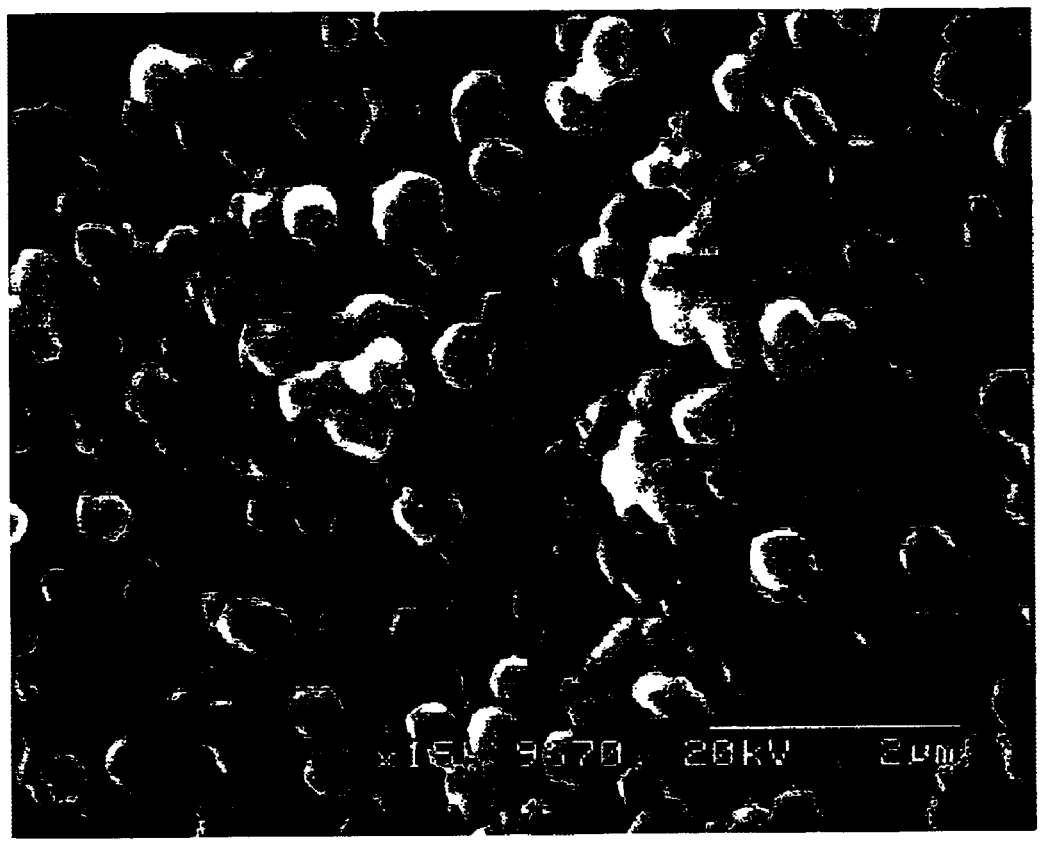

Example 8
Chemically Bonded Hydroxide Ceramics for Metal-Reinforced Ceramic Membranes The coating slurry was prepared by mixing 150 g of aluminum hydroxide powder (boehmite) and 700 g of alpha alumina powder (average particle size about 10 μm), in 1 liter of distilled water. The slurry acidity and viscosity was adjusted to approximately pH=5 using 1M nitric acid. At this stage the slurry viscosity was approximately 30 mPa.s. The slurry was deposited on stainless steel mesh substrate (approximately 40 μm mesh opening) at room temperature by spray-coating. The membrane thickness was approximately 100 μm. The membrane was subsequently dried in air at room temperature for 4 hrs and then calcined at 300° C. for 20 min, then cooled to room temperature. Subsequently the resulting steel mesh-reinforced membrane was infiltrated by 10% mono-aluminum phosphate ($Al(H_2PO_4)_2$) and reheated to 300° C. for 10 min. The resulting membranes had high porosity (approximately 40% pores by volume) and high strength due to the presence of the reinforcing stainless steel mesh. The resulting membranes were suitable for liquid or gas filtration, or as a support for other porous membranes or coatings. Typical microstructure of the resulting porous membrane is illustrated in FIG. 7, and enlarged section of the porous membrane in FIG. 8. FIG. 7 additionally illustrates fine porosity (less than 0.1 μm size pores) film on top of the large porosity film, for super-filtration.

Figure 2:

Example 9
Chemically Bonded Hydroxide Ceramic Coatings Deposited on Copper Substrates The coating slurry and surface of copper substrate were prepared as in the above example 6. Similarly, the coating slurry was deposited and heat treated as in the above example 6. The porous coatings were infiltrated by 20% monoaluminum phosphate and heated to 300° C. for 10 min. The last step of chemical bonding process was repeated two more times, with the last infiltration step using 50% monoaluminum phosphate. The resulting coatings had low porosity (approximately 3% pores by volume) and high bonding strength (43 MPa). The resulting coatings were suitable for surface modification of water-cooled copper panels for molten metal processing. Typical microstructure of the resulting coating is illustrated in FIG. 2.

Example 10
Chemically Bonded Hydroxide Ceramic Coatings Deposited on Titanium Alloy Substrates The coating slurry and surface of titanium alloy substrate were prepared as in the above example 6. Similarly, the coating slurry was deposited on titanium and heat treated as in the above example 6. The porous coatings were infiltrated by 30% monoaluminum phosphate and heated to 300° C. for 10 min. The last step of chemical bonding process was repeated two more times, with the last infiltration step using 50% phosphoric acid. The resulting coatings had low porosity (approximately 3% pores by volume) and high bonding strength (48 MPa). The resulting coatings were suitable for corrosion and oxidation protection of titanium at elevated temperatures.

Example 11
Chemically Bonded Hydroxide Ceramic Coatings Deposited on Nickel Alloy Substrates The coating slurry and surface of copper substrate were prepared as in the above example 6. Similarly, the coating slurry was deposited on high-nickel alloy and heat treated as in the above example 6. The porous coatings were infiltrated by 30% monoaluminum phosphate and heated to 300° C. for 10 min. The last step of chemical bonding process was repeated two more times using 50% phosphoric acid. The resulting coatings had low porosity (approximately 3% pores by volume) and high bonding strength (52 MPa). The resulting coatings were suitable for corrosion protection of nickel alloy at elevated temperatures in heat engine and gas turbine environments.

Example 12
Chemically Bonded Hydroxide Thick Ceramic Coatings with High Coefficient of Thermal Expansion, for Dielectric Protection The coating slurry was prepared by mixing 150 g of aluminum hydroxide powder (boehmite), 200 g calcium fluorite $CaF_2$ (average particle size about 1 μm), 100 g of alpha alumina powder (average particle size about 0.5 μm), and 450 g of alpha alumina powder (average particle size about 10 μm), in 1 liter of distilled water. The slurry acidity and viscosity was adjusted to approximately pH=4 using 1 M nitric acid. At this stage the slurry viscosity was approximately 25 mPa.s. The slurry was deposited on stainless steel solid substrate at 300° C. by spray-coating, and the substrate temperature was maintained for 10 minutes after deposition, then cooled to room temperature. Subsequently the resulting very thick (about 1–2 mm) porous coatings were infiltrated by 50% phosphoric acid and reheated to 300° C. for 10 min. The method is suitable for deposition of very thick coatings (e.g. several mm, for high voltage insulation), as the thermal stresses in the coating are minimal. This is because thermal expansion coefficient of the coating is approximately equal to that of the steel substrate.

Example 13
Chemically Bonded Hydroxide Ceramic Coatings for Surface Modification of Metallic Substrates in Contact with Organic Solids, Liquids and Gases The coating slurry and coating processing are the same as in the above example 2, on stainless steel and nickel alloy substrates. The coating was infiltrated with mono-aluminum phosphate three times. The resulting dense coating had decreased wettability by organic liquids and decreased adhesion towards organic solids, as compared to the metallic surface. The coatings were useful in decreasing organic deposits on the coated surfaces.

Example 14
Chemically Bonded Hydroxide Ceramic Coatings for Protection of Ceramic Substrates The coating slurry and coating processing are the same as in the above example 2, on silicon carbide (SiC) substrate. The resulting coatings had low porosity (approximately 5% pores by volume), medium bonding strength (26 MPa), and high surface hardness (7.1 GPa). The coatings were free of residual tension due to low value of thermal expansion coefficient of the substrate material (about $3.510^{-6}$ $K^{-1}$ for SiC). The coatings were useful for protection of the ceramic substrate from excessive oxidation at elevated temperatures.

Figure 3:

Example 15
Chemically Bonded Hydroxide Ceramic Coatings on Fiber-Reinforced, High-temperature Polymers The coating slurry was prepared as in the above example 1. The carbon fiber reinforced epoxy composite substrates were roughened, cleaned by detergent water and etched by 50% phosphoric acid. The fiber network was partially exposed through these surface preparation methods, to interlock into the subsequently deposited coating. The slurry was deposited on the substrate at room temperature by spray-coating. The coatings were subsequently dried in air at room temperature and then calcined at 250° C. for 10 min, then cooled to room temperature. Subsequently the resulting porous coatings were infiltrated by 50% monoaluminum phosphate and reheated to 300° C. for 10 min. The resulting coatings had low porosity (approximately 6% pores by volume), high bonding strength (35 MPa), and high surface hardness (6 GPa). The resulting coatings were suitable for enhanced wear, corrosion, and thermal protection of the fiber reinforced epoxy composite surface. Typical microstructure of the resulting coating is illustrated in FIG. 3.

Example 16
Use of Hydrated Alumina Slurry as a Bonding Matrix Phase of Alumina/Zirconia Composite Hydroxide Ceramic Coatings As in the above Example 2, calcined aluminum oxide is mixed with zircona particles in the aluminum hydroxide (boehmite) suspension through hand mixing, followed by ultrasonic agitation. The amount of calcined aluminum oxide plus zirconia is about 80 to 90% of calcined solids. The processing is similar as in the above Example 2. The resulting strength of the composite hydroxide coatings of the calcined aluminum oxide/zirconium oxide plus aluminum hydroxide (boehmite) is substantially higher as compared to calcined aluminum oxide/zirconium oxide only, processed in similar way. For example, after heating at 600° C. for 20 min. in air, the surface hardness of the mix of calcined aluminum oxide/zirconium oxide plus aluminum hydroxide is 0.7 GPa, as compared to 0.2 GPa of calcined aluminum oxide/zirconium oxide processed at identical conditions.

Example 17
Use of Hydrated Alumina Slurry to Seal Open Porosity of Ceramic Coatings and/or Bulk Materials This method involves the densification of ceramic coatings by infiltration of the open pores with hydroxide ceramic slurry. As in the above Example 1 hydrated alumina slurry was prepared. Adjusting pH to about 4 controlled the viscosity of the slurry. The impregnation of porous ceramic coating with the slurry was carried out at room temperature in a vacuum chamber. After impregnation, the samples were dried and dehydrated at 200° C. for 20 min and densified at 400 to 900° C. for 10 to 30 min. The processes mentioned above could be repeated several times as required. As a result, the gas permeability decreases 93% compared to untreated ceramic coatings.

Example 18
Use of Hydrated Alumina Slurry to Seal Open Porosity of Ceramic by Electrophoretic Deposition (EPD)

As in the above Example 2, hydrated alumina slurry was subject to electrophoretic deposition. Adjusting pH to about 4 controlled the viscosity of the slurry. In the electrophoresis setup, a constant potential was applied across two electrodes immersed in alumina slurry. For example, the cathode was a porous ceramic coating on the metallic substrate and platinum was used as anode. The deposition process was preformed at 0.3 to 3 V (dc constant voltage) for 10 to 40 min. After EPD impregnation, the samples were dried and dehydrated at 200° C. for 20 min and densified at 400 to 900° C. for 10 to 30 min. As a result, the porous ceramic coatings were coated by a thin film (1 to 5 $\mu$m) with no open porosity. The gas permeability decreases to 98% as compared to untreated ceramic coatings.

Example 19
Use of Hydrated Alumina Composite Slurry to Seal Open Porosity of Ceramic Coatings and/or Bulk Materials This method involves the densification of porous ceramic coatings or bulk materials by infiltration of their open pores with alumina composite slurry. As in Example 1 above, calcined alumina powder was dispersed into hydrated alumina slurry through hand mixing, followed by ultrasonic agitation. The amount of aluminum oxide is about 50 to 80% of the solid. After impregnation, the samples were dried at 50 to 300° C. for 1 to 5 hours and densified at 400 to 900° C. for 10 to 30 min. As a result, the gas permeability of impregnated porous body decreases 95% as compared to untreated body. If alumina hydroxide is absent from the composition, the coating has 40–50% open porosity, which makes the coating useless for wear and corrosion protection.

Example 20
Use of Mono-Aluminum Phosphate to Seal the Open Porosity of Ceramic Coatings and/or Bulk Materials The procedure in Example 2 was followed. The porous ceramic coatings or ceramic bulk materials were impregnated with mono-aluminum phosphate for 10 to 50 min. The impregnated samples were polymerized at 100 to 300° C. for 20 to 50 min. and then heat treated at 500 to 800° C. for 10 to 50 min. As a result of this process, surface microhardness of ceramic coating treated with mono-aluminum phosphate increases from 0.2 GPa to 2.2 GPa as compared to untreated ceramic coatings. The open porosity decreases by 95% as compared to untreated ceramic coatings. If alumina hydroxide is absent from the composition, phosphates penetrate and react with the metal substrate, leading to separation of the coating from the substrate.

Example 21
Use of Phosphoric Acid to Seal Composite Hydroxide Ceramic Coatings or Bulk Materials After the Samples were Treated with Hydrated Alumina Slurry, Alumina Composite Slurry, Mono-Alumina Phosphate, and/or EPD The hydrated alumina slurry is dried, dehydrated and subject to reaction with phosphoric acid to result in a polymerized network of mono-alumina phosphate. This application is especially suitable for adding structural integrity to the surface of porous bodies or coatings. The dried and dehydrated boehmite reacts rapidly with phosphoric acid, such that the underlying metallic substrate is not exposed to damaging phosphating reactions. As in the above Example 3, composite hydroxide ceramic coatings were impregnated by phosphoric acid for 1 to 20 min., and then were polymerized at 100 to 300° C. for 20 to 50 min. and then heat treated at 500 to 800° C. for 10 to 50 min. As a result of this process, surface microhardness of ceramic coating treated by phosphate acid increased from 0.5 GPa to 7.2 GPa compared to untreated ceramic coatings. The open porosity decreased by 99% as compared to untreated ceramic coatings. The bonding strength between ceramic coating and substrate increased from 4 MPa to more than 25 MPa as compared to untreated coatings.

Figure 5:
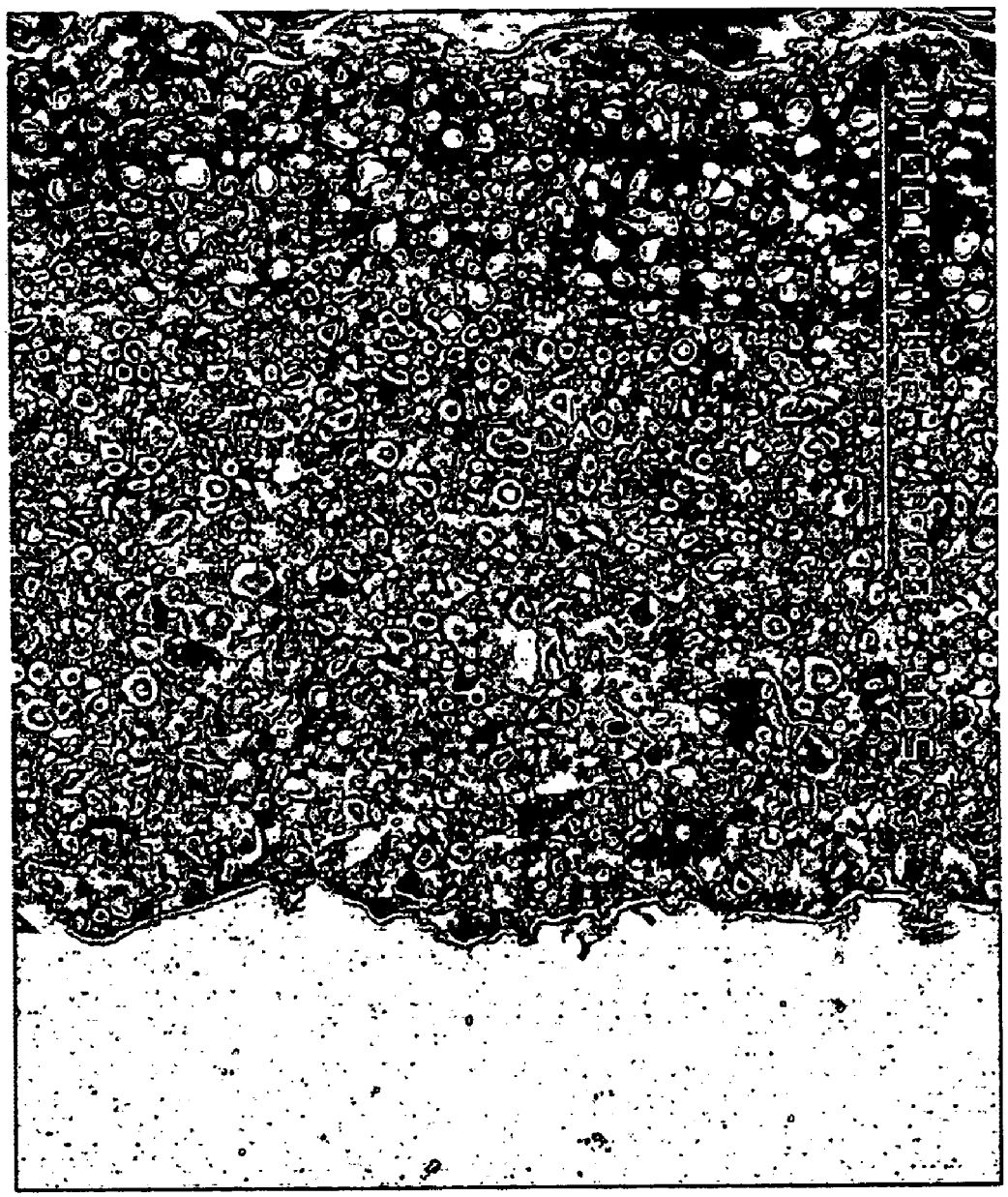

Example 22
Chemically Bonded Hydroxide Ceramic Thick, Porous Thermal Barrier Coatings Deposited on Hot Nickel Alloy Substrates The coating slurry was prepared by mixing the powders of 150 g aluminum hydroxide (boehmite), 400 g yttria—stabilized zirconia (average particle size about 6 μm), and 200 g alumina (average particle size about 0.5 μm), in 1 liter of distilled water. The slurry acidity and viscosity was adjusted to approximately pH=4 using 1 M nitric acid. At this stage, the slurry viscosity was approximately 35 mPa.s. The slurry was deposited on nickel alloy substrate at 300° C. by spray-coating, and the substrate temperature was maintained for 10 minutes after deposition, then cooled to room temperature. Subsequently, the resulting thick (approximately 0.2 mm to 2 mm) porous coating was infiltrated with 20% phosphorous acid and reheated to 300° C. for 10 min. The resulting coatings had high porosity, high thermal shock resistance and high thermal cycling resistance. The resulting coating was found useful for application as Thermal Barrier Coating (TBC) for protection of metallic components (e.g. nickel alloy components of gas turbine) from overheating. Typical microstructure of the resulting coating is illustrated in FIG. 5.

Example 23
Hydroxide Ceramic Impregnated Carbon-Fiber Composites 60 g aluminum hydroxide ceramic powder (boehmite) and 500 g calcined alpha alumina powder (Alcoa A-16) were mixed with 1 liter of deionized water and ball milled for 24 hours, to produce a hydroxide/oxide ceramic slurry. The 35% (by volume) porous carbon-carbon fiber composite samples were impregnated with the slurry in vacuum chamber for 30 min. and then the samples were fired at 300° C. for 30 min. In order to increase the alumina content in carbon-carbon composite, the impregnation and heat treatment was repeated two times. The resulting carbon-carbon-ceramic composite had oxidation resistance and wear resistance similar, as compared to the original carbon-carbon composite.

Example 24
Chemically Bonded Hydroxide Ceramic Impregnated Carbon-Carbon Fiber Composites The hydroxide alumina-calcined alumina slurry was prepared and impregnated into porous carbon-carbon fiber composite, and heat treated as in Example 23. The sample was then impregnated with 30 wt % phosphoric acid solution in water, in vacuum chamber for 30 min. and then fired again at 300° C. for 30 min. The resulting chemically bonded hydroxide ceramic carbon-carbon fiber composite had oxidation resistance three times higher and wear resistance eleven times higher as compared to the original carbon-carbon composite.

Example 25
Hydroxide/oxide/carbide Ceramic Matrix/Aluminum Composite

A mixture of 6 g aluminum hydroxide (boehmite), 30 g of calcined alpha alumina (A16 by Alcoa), 20 g of SiC powder, and 40 g of aluminum powder was ball milled for 12 hours. The composite powder was pressed at 300° C. for 20 min, at pressure of 15 MPa. The resulting consolidated ceramic-metal composite had no structural integrity and tensile strength of less than 1 MPa.

Example 26
Chemically Bonded Hydroxide/Oxide/Carbide Ceramic Matrix/Aluminum Composite A mixture of aluminum hydroxide, alpha alumina, SiC and aluminum powder was prepared as in Example 5. After ball milling, the s mixed with 30% monoaluminum phosphate at volume ratio 10/1 powder was of powder to solution, and then was pressed at 300° C. for 20 min. The resulting consolidated ceramic-metal composite had tensile strength of about 27 MPa.

As will be apparent to those skilled in the art in the light of the foregoing disclosure, many alterations and modifications are possible in the practice of this invention without departing from the spirit or scope thereof. In particular, all disclosed approaches to produce ceramic coatings might also be used to produce self-supporting, three-dimensional bulk ceramics. Accordingly, the scope of the invention is to be construed in accordance with the substance defined by the following claims.

What is claimed is:

1. A process of preparing a chemically bonded ceramic comprising:
   (a) as a first step, preparing a slurry of solvent and hydroxide ceramic;
   (b) as a second step, heat treating the hydroxide ceramic slurry at a temperature of between about 100 to 800° C. to produce a dehydrated oxide ceramic;
   (c) as a third step, impregnating the dehydrated oxide ceramic with a phosphating agent; and
   (d) as a fourth step, heat treating the phosphate impregnated oxide ceramic at a temperature between about 200° C. and about 1200° C. to seal pores in the ceramic and produce a phosphated oxide ceramic.

2. A process as claimed in claim 1, wherein the solvent is water with the pH of the slurry being between about 2 to 6, or the solvent is methyl alcohol, ethyl alcohol or isopropyl alcohol.

3. A process as claimed in claim 1 wherein the slurry in the first step (a) is a mixture of calcined alumina, hydroxide derived alumina and water which is impregnated according to step (c) with a mixture of metal phosphate and phosphoric acid to form complex amorphous or crystalline phosphates during heat treatment.

4. A process as claimed in claim 1 wherein the pores in the surface of the chemically bonded oxide ceramic are sealed by utilizing a process selected from one or more of the group consisting of hydroxide impregnation, hydroxide electrophoretic deposition, aluminum phosphate impregnation, and phosphorus acid impregnation.

5. A process as claimed in claim 1 wherein the oxide ceramic can be one or more of $SiO_2$, $Al_2O_3$, $ZrO_2$, $TiO_2$, BeO, SrO, BaO, CoO, NiO, ZnO, PbO, CaO, MgO, $CeO_2$, $Cr_2O_3$, $Fe_2O_3$, $Y_2O_3$, $Sc_2O_3$, $HfO_2$ or $La_2O_3$.

6. A process as claimed in claim 1 wherein the phosphating agent is a metal phosphate, phosphoric acid, phosphorous acid, or mixtures thereof.

7. A process as claimed in 6 wherein the metal in the phosphate can be one or more of Al, Zr, Ti, Mg, Cu, Fe, Ca, Sr, Hf or Cr, Ba, Mo, Ni, Zn, Pb or Sn.

8. A process as claimed in claim 5 wherein a calcined ceramic filler comprised of powders or fibers of oxides, carbides, nitrides, borides, sulphides. fluorides or mixtures thereof, is included in the slurry of step (a).

9. A process as claimed in claim 3 wherein the hydroxide derived alumina is partially amorphous or crystalline alumina produced through thermal decomposition of boehmite-type hydrated alumina AlOOH, or equivalently aluminum oxide monohydrate $Al_2O_3H_2O$.

10. A process as claimed in claim 1 wherein in step (a) a substrate is immersed slurry to coat the substrate, the substrate is withdrawn from the slurry and the coating on the substrate is dried at a temperature of 50 to 400° C., before proceeding with step (b).

11. A process as claimed in claim 10 wherein pores in the surface of the ceramic coating on the substrate are sealed by treating the ceramic coating with phosphoric acid for about 1 to 20 minutes, polymerizing the phosphoric acid treated ceramic coating at a temperature of about 100 to 300° C. for 20 to 50 minutes; and subsequently further treating the coating at a temperature of 500 to 800° C. for about 10 to 50 minutes.

12. A process as claimed in claim 10 wherein in step (a) the ceramic slurry is produced by mixing a hydroxide solution with metal oxide ceramic powder; the ceramic hydroxide slurry is applied to the substrate to produce a ceramic coated substrate, the ceramic coated substrate is heated to a temperature of up to about 1000° C. to produce a ceramic metal oxide film substrate; and surface pores of the ceramic coating are sealed with a phosphorus containing ceramic sealant.

13. A process as claimed in claim 10 wherein the surface sealing process (d) is selected from the group of processes consisting of hydroxide impregnation, hydroxide electrophoretic deposition, aluminum phosphate impregnation and phosphorus acid impregnation.

14. A process as claimed in claim 10 wherein the hydroxide slurry solution comprises aluminum monohydrate (boehmite) and water, which produces an aluminium hydroxide derived oxide coated substrate.

15. A process as claimed in claim 14 wherein the aluminum hydroxide derived oxide coated substrate is treated with phosphoric acid and the phosphoric acid is reacted with the ceramic coating at a temperature of at least 200° C. for at least 2 min.

* * * * *